United States Patent [19]

Sprague et al.

[11] Patent Number: 4,503,241
[45] Date of Patent: Mar. 5, 1985

[54] 7-OXABICYCLOHEPTANE PROSTAGLANDIN INTERMEDIATES

[75] Inventors: Peter W. Sprague, Pennington; James E. Heikes, East Windsor, both of N.J.

[73] Assignee: E. R. Squibb & Sons, Inc., Princeton, N.J.

[21] Appl. No.: 494,232

[22] Filed: May 13, 1983

[51] Int. Cl.³ .......................................... C07D 307/88
[52] U.S. Cl. ................................................... 549/459
[58] Field of Search ......................................... 549/459

[56] References Cited

U.S. PATENT DOCUMENTS 4,143,054  3/1979  Sprague .............................. 549/459

OTHER PUBLICATIONS

Orchin et al., The Vocabulary of Organic Chem., Wiley and Sons, (1980), 122,130,131,144.
Haslanger et al., Synthesis, Oct. 1981, pp. 801–802.
Woodward et al., J.A.C.S., vol. 95(20), (1973), pp. 6853–6855.
Mitra, The Synthesis of Prostaglandins, Wiley, 1977, p. 12.
Sprague et al., Advances in Prostaglandin and Thromboxane Research, vol. 6, pp. 493–496, (1980).

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane prostaglandin intermediates are provided having the general structure

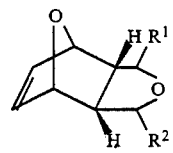

wherein one of $R^1$ and $R^2$ is

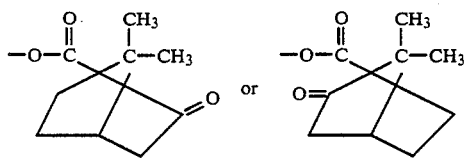

and the other is hydrogen.

A method for preparing the above intermediates is also provided. The final products are used in the treatment of thrombolytic disease.

7 Claims, No Drawings

7-OXABICYCLOHEPTANE PROSTAGLANDIN INTERMEDIATES

FIELD OF THE INVENTION

The present invention relates to optically active intermediates for use in preparing 7-oxabicycloheptane prostaglandin analogs and to a method for preparing such interemdiates.

BACKGROUND OF THE INVENTION

U.S. Pat. No. 4,413,054 to Sprague dated Mar. 6, 1979 discloses 7-oxabicycloheptane and 7-oxabicycloheptene prostaglandin analogs which are prepared by the following methods.

In a first method maleic anhydride is made to react with an unsubstituted or substituted furan of the formula

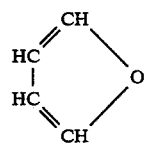

to form a compound of the formula

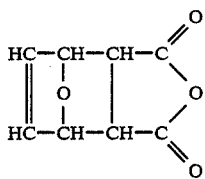

which is reduced to form

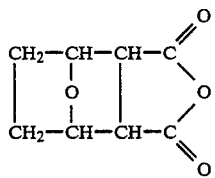

The above compound is then further reduced to form

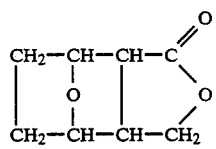   A

Treatment of the above compound with diisobutylaluminum hydride or diisobutylborane yields

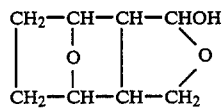   B

Submitting compound A to Wittig reaction conditions produces

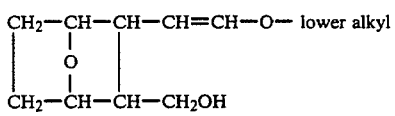   C

Compound C is then acylated and then hydrolyzed to form the aldehyde

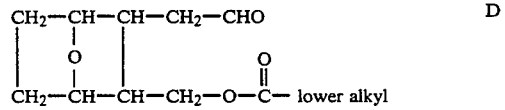   D

All of the above compounds are in the form of racemic mixtures.

Aldehyde D is subjected to a Wittig reaction to form a compound of the structure

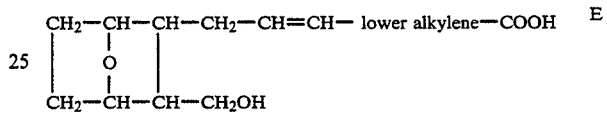   E which is esterified to form the corresponding lower alkyl ester. The hydroxymethyl group in the 3-position of the ester is then oxidized to obtain the aldehyde

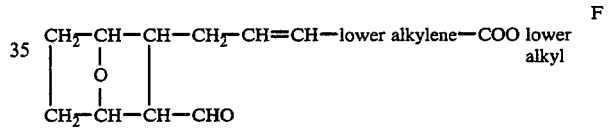   F

Aldehyde F which is in the form of a racemic mixture is employed to form 7-oxabicycloheptane prostaglandin analogs.

DESCRIPTION OF THE INVENTION

In accordance with the present invention, a method is provided for forming the aldehyde D(a) also depicted graphically as

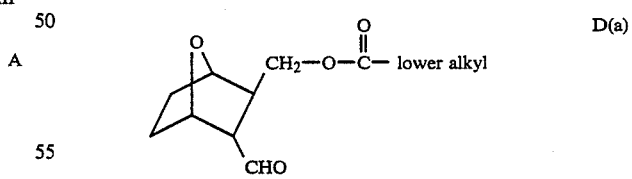   D(a)

in the form of its optically active isomer as opposed to a racemic mixture of two enantiomers as disclosed by Sprague in U.S. Pat. No. 4,143,054. The optically active aldehyde D(a) is then employed to form optically active 7-oxabicycloheptane prostaglandin analogs, for example, using the technique described by Sprague in U.S. Pat. No. 4,143,054.

In carrying out the method of the invention as described hereinafter several novel optically active intermediates are formed having the following formula

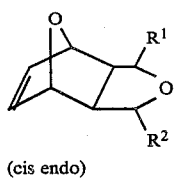

(cis endo)

depicted graphically as

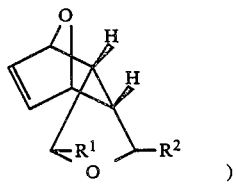

wherein one of R¹ and R² is

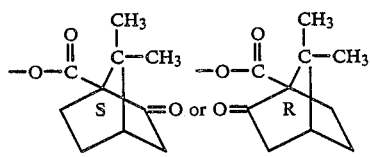

and the other is H, and includes the following compounds:

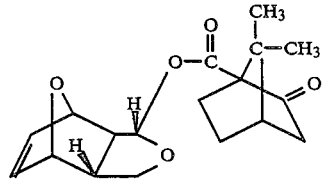

(cis endo)

[1S—[1α(1S),3aα,4β,7β,7aα]]-1,3,3a,4,7,7a-
Hexahydro-1-[[2-oxo-7,7-dimethylbicyclo[2.2.1]-
heptane]carboxyl]-4,7-epoxyisobenzofuran

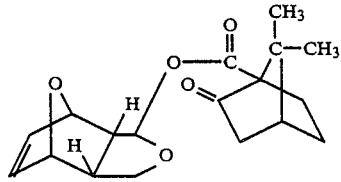

(cis endo)

[1S—[1α(1R),3aα,4β,7β,7aα]]-1,3,3a,4,7,7a-
Hexahydro-1-[[2-oxo-7,7-dimethylbicyclo[2.2.1]-
heptane]carboxyl]-4,7-epoxyisobenzofuran

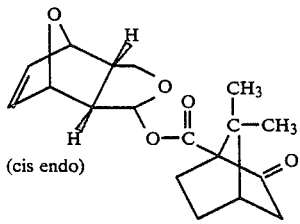

(cis endo)

I

II

III

IV

-continued
[1R—[1α(1S),3aα,4β,7β,7aα]]-1,3,3a,4,7,7a-
Hexahydro-1-[[2-oxo-7,7-dimethylbicyclo[2.2.1]-
heptane]carboxy]-4,7-epoxyisobenzofuran

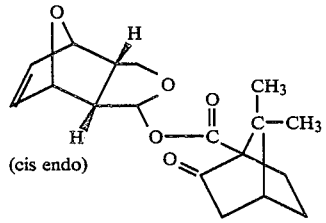

(cis endo)

V

[1R—[1α(1R),3aα,4β,7β,7aα]]-1,3,3a,4,7,7a-
Hexahydro-1-[[2-oxo-7,7-dimethylbicyclo[2.2.1]-
heptane]carboxy]-4,7-epoxyisobenzofuran The method of the present invention for forming optically active or chiral intermediates for use in preparing optically active 7-oxabicycloheptane prostaglandin analogs includes the step of reacting the racemic hemiacetal

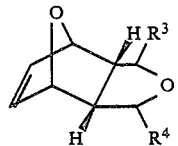

G wherein one of R³ and R⁴ is OH and the other is H (prepared as described in U.S. Pat. No. 4,143,054) with l-ketopinic acid halide, such as the chloride (prepared as described in U.S. Pat. No. 4,235,891) employing a molar ratio of G:ketopinic acid chloride of about 0.5:1 to about 1:1, in the presence of 4-dimethylamino-pyridine or 4-diethylaminopyridine and an inert solvent such as pyridine or dichloromethane to form a diastereomeric mixture of the ketopinate esters II and IV (where l-ketopinic acid halide is used). The mixture of diastereomers of formula I is recrystallized, for example, from isopropyl ether to form the optically active isomer II. The reaction sequence for preparing the optically active antipodes or mirror images of compounds of formulae II and IV, namely compounds of formulae III and V, respectively, may be prepared following the above reaction sequence except that d-ketopinic acid halide is employed in place of the corresponding l-isomer.

The optically active ketopinate II (IV) or III (V) may then be subjected to ester hydrolysis, for example, by reacting the ketopinate with lithium hydroxide/hydrogen peroxide, to form the optically active hemiacetal

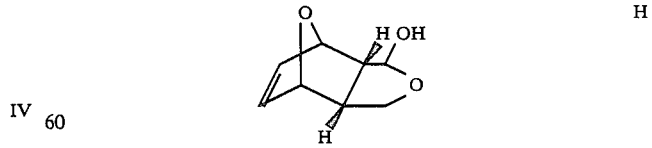

H

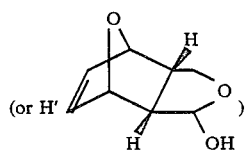

(or H')

which then undergoes dimethylhydrazone formation by reaction with unsymdimethylhydrazine to form the dimethylhydrazone

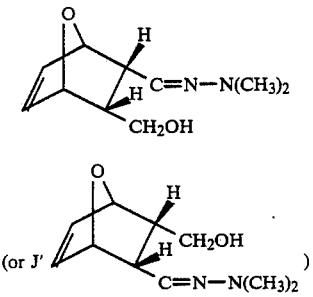

Compound J is then acetylated to form

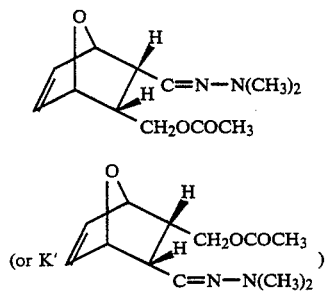

which is reduced by reaction with hydrogen in the presence of a catalyst such as palladium on carbon to form

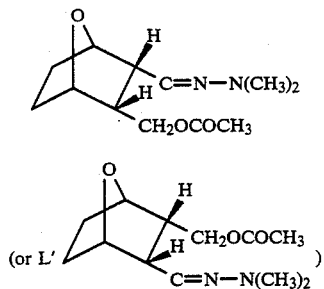

Compound L is then made to undergo hydrazone hydrolysis, for example, by reacting L with cupric chloride dihydrate in the presence of a solvent such as tetrahydrofuran to form the aldehyde

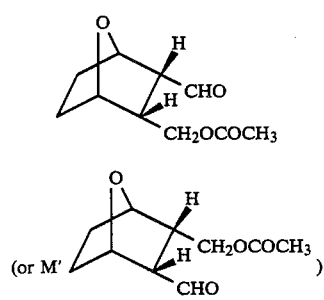

The prostaglandin aldehyde analog M (and M' where d-ketopinic acid halide is used) may then be employed to prepare 7-oxabicycloheptane prostaglandins following the procedure as set out in U.S. Pat. No. 4,143,054 to Sprague. Such prostaglandin derivatives are useful in the treatment of thrombolytic disease as explained in the above Sprague patent.

The following Examples represent preferred embodiments of the present invention.

EXAMPLES 1 AND 2

[1S-[1α(1S),3aα,4β,7β,7aα]]-1,3,3a,4,7,7a-Hexahydro-1-[[2-oxo-7,7-dimethylbicyclo[2.2.1]heptane]carboxyl]-4,7-epoxyisobenzofuran (Example 1) and
[1R-[1α(1S),3aα,4β,7β,7aα]]-1,3,3a,4,7,7a-Hexahydro-1-[[2-oxo-7,7-dimethylbicyclo[2.2.1]heptane]carboxyl]-4,7-epoxyisobenzofuran (Example 2)

A solution of (endo)-1,3,3a,4,7,7a-hexahydro-4,7-epoxyisobenzofuran-1-ol (prepared as described in Example 14 of U.S. Pat. No. 4,143,054) (53.2 g, 343 mmoles), l-ketopinic acid chloride (70 g, 350 mmoles) and 4-dimethylaminopyridine (1 g, 8 mmoles) in pyridine (500 ml) was stirred at room temperature for 18 hours. The reaction mixture was concentrated in vacuo. The residue was diluted with water and extracted with dichloromethane (3×300 ml). The combined extracts were dried over magnesium sulfate and concentrated in vacuo and found to contain a mixture of Examples 1 and 2 isomers. The crude product was recrystallized 4 times from isopropyl ether to yield 19 g of title Example 1 product, m.p. 123°–125° C.

$[\alpha]_D = +58°$ c=1 CHCl$_3$.

TLC: silica gel; ether/hexane (1:1); R$_f$=0.2; vanillin spray+heat.

EXAMPLE 3

[1R-(1α,2α,3α,4α)]-3-(Acetoxymethyl)-7-oxabicyclo[2.2.1]heptane-2-carboxaldehyde

A.

[1S-[3aα,4β,7β,7aα]]-1,3,3α,4,7,7a-Hexahydro-4,7-epoxyisobenzofuran-1-ol

A solution of Example 1 compound (6.36 g, 20 mmole) in tetrahydrofuran (100 ml) was treated with 1 normal lithium hydroxide (20 ml, 20 mmole) and 30% hydrogen peroxide (0.23 ml, 20 mmole) then stirred vigorously in a Morton flask at room temperature for 2 hours. TLC after this time indicated complete absence of starting material. The solution was quenched with 5% sodium thiosulfate (5 ml) then saturated with sodium chloride and extracted with chloroform (10×50 ml). The combined extracts were dried over magnesium sulfate and concentrated. The residue was recrystallized from benzene/cyclohexane to yield 3 g of desired hemiacetal, m.p. 99°–100° C.

TLC: silica gel; ethyl acetate/dichloromethane (1:1); R$_f$=0.2; vanillin spray+heat.

$[\alpha]_D = +67°$, c=10 mg/ml CHCl$_3$.

B.

[1R-(1α,2α,3α,4α)]-3-(Hydroxymethyl)-7-oxa-5-bicyclo[2.2.1]heptene-2-carboxaldehyde 1,1-dimethylhydrazone A solution of title B hemiacetal (2.8 g, 18 mmole) and unsym-dimethylhydrazine (2.2 g, 37 mmole) in dichloromethane (50 ml) was stirred at room temperature overnight. The reaction mixture was then concentrated in vacuo to yield 3.5 g of desired title B product.

TLC: silica gel; ether; R$_f$=0.15; vanillin spray+heat.

C.
[1R-(1α,2α,3α,4α)]-3-(Acetoxymethyl)-7-oxa-5-bicyclo[2.2.1]heptene-2-carboxaldehyde 1,1-dimethylhydrazone A solution of title B compound (11.5 g, 59 mmole), trimethylamine (61 g, 600 mmoles) and 4-dimethylaminopyridine (0.465 g, 3.8 mmoles) in acetic anhydride (31 g, 300 mmoles) was stirred at room temperature for 2 hours. After this time TLC indicated complete conversion to the acetate. The mixture was concentrated in vacuo. The residue was poured into ice water and extracted with methylene chloride. The organic layer was dried over magnesium sulfate and concentrated in vacuo. The residue was chromatographed on LP-1 silica (1500 ml) eluting with ether/hexane (1:1) to yield 14 g of title C compound.

TLC: silica gel; ether; $R_f=0.4$; vanillin spray+heat.

D.
[1R-(1α,2α,3α,4α)]-3-(Acetoxymethyl)-7-oxabicyclo[2.2.1]heptane-2-carboxaldehyde 1,1-dimethylhydrazone A solution of title C compound (2.1 g, 8.8 mmole) in ethyl acetate (100 ml) was treated with 10% Pd/C (200 mg) and stirred under one atmosphere of hydrogen until 200 ml of hydrogen had been consumed. The mixture was filtered through celite and concentrated to yield 2.1 g of title D compound. CMR indicated that the product still contained 5% of the undesired trans isomer.

TLC: silica gel; ether; $R_f=0.4$; vanillin spray+heat.

E.
[1R-(1α,2α,3α,4α)]-3-(Acetoxymethyl)-7-oxabicyclo[2.2.1]heptane-2-carboxaldehyde A solution of title D compound (2.1 g, 8.8 mmole) in tetrahydrofuran (130 ml) was treated with a solution of cupric chloride dihydrate (2.98 g, 17.6 mmole) in pH=7 phosphate buffer (140 ml). The mixture was stirred at room temperature for 2 hours, then concentrated in vacuo to approximately 150 ml. The mixture was diluted with dichloromethane (300 ml) and filtered through celite. The filtrate was washed with 5% sodium bicarbonate, dried over magnesium sulfate, and concentrated in vacuo to produce title aldehyde.

EXAMPLES 4 AND 5

[1S-[1α(1R),3aα,4β,7β,7aα]]-1,3,3a,4,7,7a-Hexahydro-1-[[2-oxo-7,7-dimethylbicyclo[2.2.1]heptane]carboxyl]-4,7-epoxyisobenzofuran (Example 4) and
[1R-[1α(1R),3aα,4β,7β,7aα]]-1,3,3a,4,7,7a-Hexahydro-1-[[2-oxo-7,7-dimethylbicyclo[2.2.1]heptane]carboxyl]-4,7-epoxyisobenzofuran (Example 5)

A solution of (endo)-1,3,3a,4,7,7a-hexahydro-4,7-epoxyisobenzofuran-1-ol (12.7 g, 82.5 mmole) d-ketopinic acid (15 g, 82 mmole), and 4-dimethylaminopyridine (10.1 g, 82 mmole) in anhydrous dichloromethane (400 ml) was treated with dicyclohexylcarbodiimide (DCC) (17.1 g, 82 mmole) and stirred at room temperature for 3 days. The reation mixture was then filtered. The filtrate was washed with 5% potassium bisulfate, 5% sodium bicarbonate and water. The dichloromethane solution was dried over magnesium sulfate and concentrated in vacuo. The residue was chromatographed on LP-1 silica gel (600 ml) eluting with dichloromethane and ether/dichloromethane (1:4). Fractions containing the desired ester (Example 4) and Example 5 ester were combined and concentrated in vacuo. The solid residue was recrystallized 3 times from isopropyl ether to yield 5.5 g of optically active title Example 4 compound, m.p. 135°–138° C.

$[\alpha]_D=-57°$, c=10 mg/ml CHCl$_3$.

TLC: silica gel; ether/hexane (1:1), $R_f=0.2$; vanillin spray+heat.

EXAMPLE 6

[1S-(3aα,4β,7β,7aα)]-1,3,3a,4,7,7a-Hexahydro-4,7-epoxyisobenzofuran-1-ol

A solution of Example 4 compound (5.5 g, 17.3 mmole) in tetrahydrofuran (90 ml) was treated with 1N lithium hydroxide solution (17.3 ml, 17.3 mmole) and 30% hydrogen peroxide (0.2 ml, 17.3 mmole) then stirred vigorously in a Morton flask at room temperature for 2 hours. After this time, TLC indicated complete absence of starting material. The solution was quenched with 5% sodium thiosulfate solution (5 ml), saturated with sodium chloride, and extracted with chloroform (10×50 ml). The combined extracts were dried over magnesium sulfate and concentrated in vacuo. The residue was recrystallized from benzene to yield 2 g of title compound, m.p. 105°–109° C.

TLC: silica gel; ethyl acetate/dichloromethane (1:1); $R_f=0.2$; vanillin spray+heat.

$[\alpha]_D=-67°$, c=10 mg/ml CHCl$_3$.

B.
[1S-(1α,2α,3α,4α)]-3-(Hydroxymethyl)-7-oxa-5-bicyclo[2.2.1]heptene-2-carboxaldehyde 1,1-dimethylhydrazone A solution of title A compound (2 g, 13 mmole) and unsymdimethylhydrazine (1.6 g, 27 mmole) in dichloromethane (75 ml) was stirred overnight at room temperature. The reaction mixture was then concentrated in vacuo to yield 2.5 g of title B compound.

TLC: silica gel; ether; $R_f=0.15$; vanillin spray+heat.

C.
[1S-(1α,2α,3α,4α)]-3-(Acetoxymethyl)-7-oxa-5-bicyclo[2.2.1]heptene-2-carboxaldehyde 1,1-dimethylhydrazone A solution of title B compound (2.5 g, 12.7 mmole) in acetic anhydride (15 ml) was stirred at room temperature for 8 hours then concentrated in vacuo. The residue was dissolved in ether and washed with 5% sodium bicarbonate and brine. The ether layer was chromatographed on LP-1 silica gel (500 ml) eluting with ether/pentane (1:1) to yield 775 mg of title C compound.

TLC: silica gel; ether; $R_f=0.4$; vanillin spray+heat.

D.
[1S-(1α,2α,3α,4α)]-3-(Acetoxymethyl)-7-oxabicyclo[2.2.1]heptene-2-carboxaldehyde 1,1-dimethylhydrazone A solution of title C compound (775 mg, 3.26 mmole) in ethyl acetate (100 ml) was treated with 10% Pd/C (100 mg) and stirred under one atmosphere of hydrogen until 75 ml of hydrogen had been consumed. The mixture was filtered and concentrated in vacuo to yield 775 mg of title D compound.

TLC: silica gel; ether; $R_f=0.4$; vanillin spray+heat.

E.

[1S-(1α,2α,3α,4α)]-3-(Acetoxymethyl)-7-oxabicyclo[2.2.1]heptane-2-carboxaldehyde A solution of title D compound (775 mg, 3.2 mmole) in tetrahydrofuran (48 ml) was treated with a solution of cupric chloride dihydrate (1.1 g, 6.5 mmole) in pH=7 phosphate buffer (52 ml). The mixture was stirred at room temperature for 2 hours, then concentrated in vacuo to approximately one-half its original volume. The mixture was diluted with dichloromethane (100 ml) and filtered through celite. The filtrate was washed with 5% sodium bicarbonate, dried over magnesium sulfate and concentrated in vacuo to give title product.

What is claimed is:

1. An optically active cis endo isomer having the structure

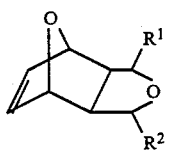

wherein one of R¹ and R² is

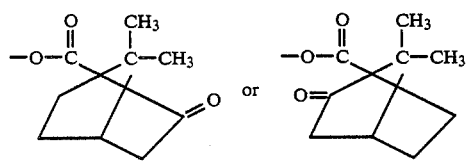

and the other is H.

2. The compound as defined in claim 1 wherein R¹ is

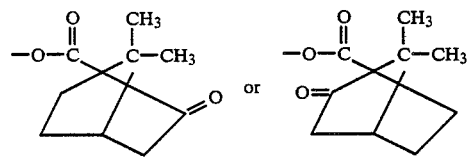

3. The compound as defined in claim 1 wherein R² is

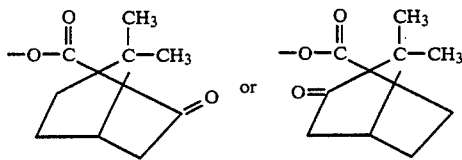

4. The compound as defined in claim 1 having the structure

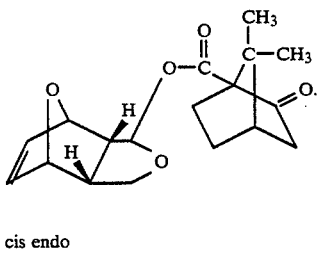

cis endo

5. The compound as defined in claim 1 having the structure

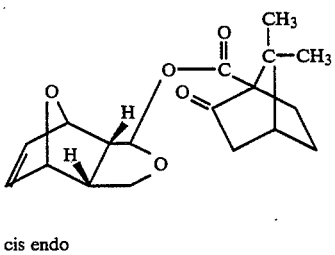

cis endo

6. The compound as defined in claim 1 having the structure

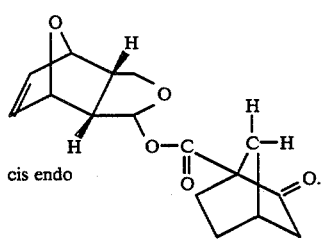

cis endo

7. The compound as defined in claim 1 having the structure

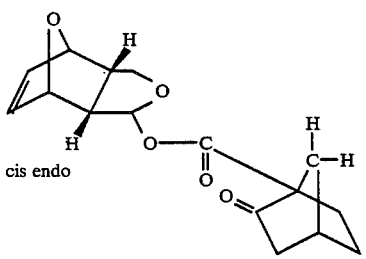

cis endo

* * * * *